(12) United States Patent
Woelfert et al.

(10) Patent No.: US 8,088,944 B2
(45) Date of Patent: *Jan. 3, 2012

(54) METHOD FOR THE PURIFICATION OF ISOCYANATES

(75) Inventors: Andreas Woelfert, Bad Rappenau (DE);
Hans-Juergen Pallasch, Kallstadt (DE);
Eckhard Stroefer, Mannheim (DE);
Heinrich-Josef Blankertz, Forst (DE)

(73) Assignee: BASF SE, Ludwigshafen (DE)

( * ) Notice: Subject to any disclaimer, the term of this patent is extended or adjusted under 35 U.S.C. 154(b) by 845 days.

This patent is subject to a terminal disclaimer.

(21) Appl. No.: 11/523,556

(22) Filed: Sep. 20, 2006

(65) Prior Publication Data

US 2007/0015934 A1    Jan. 18, 2007

Related U.S. Application Data

(62) Division of application No. 10/539,131, filed as application No. PCT/EP03/14280 on Dec. 16, 2003, now Pat. No. 7,358,388.

(30) Foreign Application Priority Data

Dec. 19, 2002    (DE) .................. 102 60 092

(51) Int. Cl.
*C07C 291/00*    (2006.01)
*C07C 249/00*    (2006.01)

(52) U.S. Cl. ........................... 560/352; 560/347
(58) Field of Classification Search .............. None
See application file for complete search history.

(56) References Cited

U.S. PATENT DOCUMENTS

| | | | |
|---|---|---|---|
| 3,140,305 A | 7/1964 | Lowenstein | |
| 3,410,888 A | 11/1968 | Hammond | |
| 3,471,543 A | 10/1969 | Sayigh | |
| 4,216,063 A | 8/1980 | Ailloud et al. | |
| 4,713,476 A | 12/1987 | Merger et al. | |
| 5,087,739 A | 2/1992 | Bohmholdt et al. | |
| 5,136,086 A | 8/1992 | Nagata et al. | |
| 5,386,053 A | 1/1995 | Otterbach et al. | |
| 5,962,728 A * | 10/1999 | Mason et al. ............. | 560/352 |

FOREIGN PATENT DOCUMENTS

| | | |
|---|---|---|
| DE | 102 45 584 | 4/2004 |
| EP | 0 018 586 | 11/1980 |
| EP | 0 355 443 | 2/1990 |
| EP | 0 566 925 | 10/1993 |
| EP | 0 568 782 | 11/1993 |
| EP | 0 976 723 | 2/2000 |

OTHER PUBLICATIONS

Perry, R.H.; Green, D.W. (1997). Perry's Chemical Engineers' Handbook (7th Edition). McGraw-Hill pp. 11-1-1-18.*

* cited by examiner

*Primary Examiner* — Karl J Puttlitz
(74) *Attorney, Agent, or Firm* — Oblon, Spivak, McClelland, Maier & Neustadt, L.L.P.

(57) ABSTRACT

Isocyanates are prepared by a process in which a product stream from the isocyanate synthesis is purified.

11 Claims, 2 Drawing Sheets

METHOD FOR THE PURIFICATION OF ISOCYANATES

CROSS REFERENCE TO RELATED APPLICATIONS

The present application is a Divisional Application of U.S. patent application Ser. No. 10/539,131, filed Jun. 16, 2005, which is a National Stage (371) of International Application No. PCT/EP03/14280 filed on Dec. 16, 2003.

BACKGROUND

The present invention relates to a process for the preparation of isocyanates by purifying a product stream from the isocyanate synthesis.

Here, isocyanates are understood as meaning compounds having 1, 2 or more isocyanate groups (mono-, di- or polyisocyanates), preferably diisocyanates.

The novel process is suitable for all customary (cyclo) aliphatic and aromatic isocyanates or a mixture of two or more such isocyanates. Diisocyanates, for example monomeric methylene di(phenylisocyanate) (MDI), tolylene diisocyanate (TDI), R,S-1-phenylethyl isocyanate, 1-methyl-3-phenylpropyl isocyanate, naphthyl diisocyanate (NDI), n-pentyl isocyanate, 6-methyl-2-heptane isocyanate, cyclopentyl isocyanate, hexamethylene diisocyanate (HDI), isophorone diisocyanate (IPDI), 2,4 and 2,6-diisocyanatomethylcyclohexane ($H_6$TDI) and the isomer mixtures thereof, o-, m- or p-xylene diisocyanate (XDI), diisocyanatocyclohexane (t-CHDI), di(isocyanatocyclohexyl)methane ($H_{12}$MDI), tetramethyl-m-xylylene diisocyanate (m-TMXDI), 1,3-bis(isocyanatomethyl)cyclohexane ($H_6$XDI), diisocyanatocyclohexane (t-CHDI), 1,6-diisocyanato-2,2,4,4-tetramethylhexane, 1,6-diisocyanato-2,2,4-trimethylhexane and mixtures thereof (TMDI), are preferred.

The process for purifying TDI, monomeric MDI, HDI, IPDI, $H_6$TDI, $H_{12}$MDI, XDI, t-CHDI and NDI is particularly preferably used.

The literature describes various processes for the preparation of pure isocyanate.

U.S. Pat. No. 3,410,888 describes a process for isolating and purifying isocyanates. The process comprises the following steps: first, the reaction of a corresponding diamine with phosgene and the distillative separation of a part of the isocyanate thus prepared in the course of the solvent separation, secondly the transfer of the distillation residue (bottom product) into a second distillation apparatus (vessel), over the internal surface of which the residue is distributed as a thin film and the temperature and pressure of which are sufficient to effect vaporization of the isocyanate, and thirdly the removal of the vapor, which is substantially rich in isocyanate, from this second distillation apparatus.

The vapor is condensed and gives the isocyanate. Rising-film evaporators, falling-film evaporators and the like are mentioned as possible distillation apparatuses. The chosen solvent in the isocyanate synthesis usually has a lower boiling point than the isocyanate, preferably at least 30° C. lower. In the case of smaller boiling point differences, however, a part of the isocyanate prepared is separated off together with the solvent in the solvent separation. This is followed by the distillation of the crude isocyanate obtained as a residue, said distillation being effected in a thin-film evaporator. The partial isolation of the isocyanate in the solvent separation has the advantage that undesired medium boilers (possibly colored impurities or components whose boiling point is between that of the isocyanate and that of the solvent) are concomitantly separated off in the solvent separation. The mixture of the partly isolated isocyanate and the solvent is then recycled as a feedstock stream to the solvent separation, or it is fed to a separate evaporation or fractional distillation for concentrating the isocyanate. The latter is then recycled as a feed into the solvent separation.

The disadvantage of this process is that, owing to the evaporation in two steps in the case of isomeric isocyanates, e.g. TDI or MDI, fractions of different composition are obtained as a result of the different volatilities of the isomers. The purity of the isocyanates obtained moreover does not meet the present day requirements since low boilers are still contained. In addition, the product is lost via the high-boiling residue since the residue must be flowable in order to be capable of being transported out of the evaporator.

The prior German Application with the application number 10245584.8 and the date of filing of Sep. 27, 2002 describes a process for the preparation of isocyanates, the reaction discharge being present in the form of a suspension which contains the isocyanate to be prepared in the form of a liquid and carbamoyl chloride as a solid, in which process the suspension is worked up in a film evaporator. This film evaporator preferably has no moving parts, as, for example, a falling-film evaporator. The working-up can also be effected in a plurality of pressure stages in two or more film evaporators connected in series, the first film evaporator operating at a pressure of from 0.5 to 25 bar and the pressure of the second being from 0.01 to 1 bar lower than that of the first.

U.S. Pat. No. 5,962,728 describes the use of a thin-film evaporator in combination with a paddle dryer and a low boiler separation column. The crude isocyanate is fed to a thin-film evaporator. In the thin-film evaporator, the pure isocyanate is separated from the high-boiling, polymeric tar, the separation not being complete in order to obtain the tar in a form with sufficiently low viscosity. The tar stream still containing residues of the desired product is fed to a paddle dryer, in which the residual isocyanate is evaporated off from the tar. The isocyanate vapor, which still contains low-boiling impurities, is finally subjected to removal of the low boilers by distillation. The process is distinguished by the fact that the paddle dryer simultaneously has a heating zone and a cooling zone.

A disadvantage of the process is that the isocyanate stream leaving the arrangement is always taken off as bottom product and is therefore exposed to high thermal stresses, which leads to losses of NCO groups by oligomerization or polymerization of diisocyanate, since such high boilers are not separated off.

U.S. Pat. No. 3,140,305 describes the use of a horizontal thin-film evaporator for recovering aromatic diisocyanates. A disadvantage of the process is that the TDI recovered still contains low-boiling impurities, which complicates the direct use of the reaction discharge as a starting material in the polyurethane preparation. In addition, the desired product is lost from the high-boiling residue.

U.S. Pat. No. 4,216,063 describes the recovery of tolylene diisocyanate (TDI) in a thin-film evaporator at a wall temperature of from 210 to 250° C. and a pressure of from 1 to 50 mm Hg with a minimum residence time of 15 minutes. A disadvantage of the process is that the TDI recovered still contains low-boiling impurities, which complicates the direct use of the reaction discharge as a starting material in the polyurethane preparation.

SUMMARY

It is an object of the present invention to provide a process for the preparation of pure isocyanate by purifying a crude isocyanate stream, in which the desired pure isocyanate can be obtained with very high purity and high yield, it simultaneously being intended to keep the complexity of the apparatus and the energy demand as low as possible.

We have found that this object is achieved by a process for purifying isocyanates, in which:

a) a stream (1) containing isocyanate, higher- and lower-boiling components and unvaporizable residue is separated, in a distillation comprising at least one theoretical plate, into a part-stream (2) which contains an unvaporizable residue and isocyanate and into a vapor stream (3) containing isocyanate and low boilers, b) the unvaporizable residue in the part-stream (2) is kept separate from the vapor stream (3) and/or from streams which at least partly contain the vapor stream (3), c) at least one further isocyanate-containing vapor stream (4) and a stream (8) substantially containing unvaporizable residue are separated from the part-stream (2) and d) the isocyanate-containing vapor stream or streams (4) and the vapor stream (3) from a) are separated into three individual streams (5, 6, 7) having different boiling ranges by distillation, the lowest-boiling stream (5) containing a substantial part of the low boiler content of the crude isocyanate stream (1), the highest-boiling stream (7) containing a substantial part of the high boiler content of the crude isocyanate stream (1) and the medium-boiling stream (6) substantially containing desired product.

BRIEF DESCRIPTION OF THE DRAWINGS

Exemplary embodiments of the present invention are described herein with reference to the following figures, wherein.

DETAILED DESCRIPTION OF EXEMPLARY EMBODIMENTS

Figure 1:
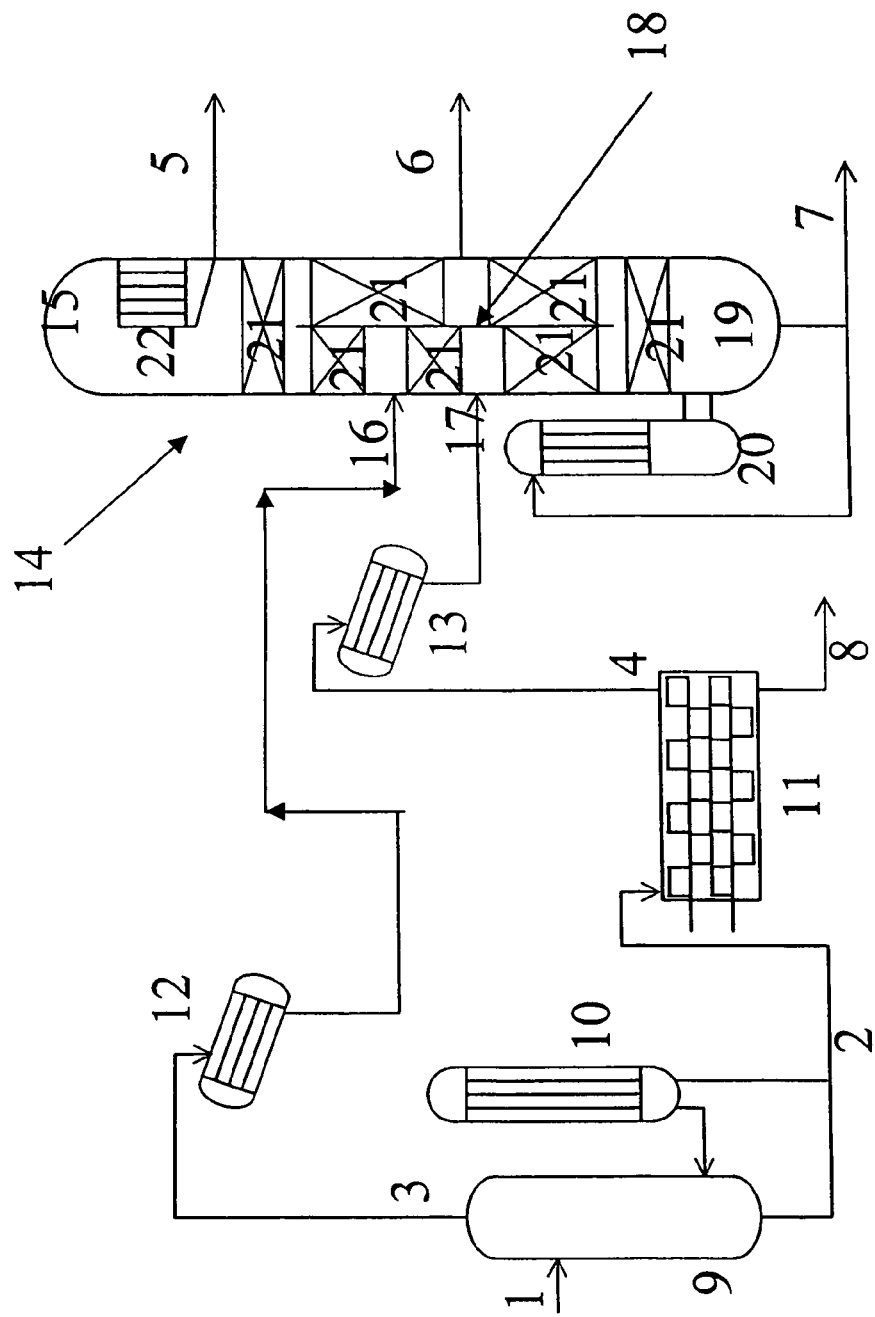
FIG. 1 is a schematic depiction of a first exemplary isocyanate purification system according to the present invention.

The process by which the crude isocyanate used has been obtained, for example by phosgenation of an amine, by phosgenation of an amine hydrochloride or of a carbamate salt, by the urea process, as described, for example, in EP 18 586, EP 566 925, EP 355 443 or EP 568 782, or by reaction of the parent amine with dialkyl carbonates, as described, for example, in EP-A2 976 723, is unimportant for the novel process. The isocyanate is preferably prepared by phosgenation.

The isocyanates are usually prepared by reacting the corresponding primary amine or its hydrochloride with an excess of phosgene. This process usually takes place in the liquid phase in a solvent or in the gaseous phase. The process is preferably carried out in the liquid phase.

The solvent used is usually a solvent which has a lower boiling point than the isocyanate, e.g. chlorobenzene, o- or p-dichlorobenzene, trichlorobenzene, chlorotoluenes, chloroxylenes, chloroethylbenzene, chloronaphthalenes, chlorobiphenyls, methylene chloride, perchloroethylene, toluene, xylenes, hexane, decahydronaphthalene, diethyl isophthalate (DEIP) and other carboxylic esters, as mentioned, for example, in U.S. Pat. No. 5,136,086, column 3, lines 3 to 18, tetrahydrofuran (THF), dimethylformamide (DMF), benzene and mixtures thereof. The isocyanate prepared or a stream of the process may also be used as a solvent. Chlorobenzene and dichlorobenzene are particularly preferred. The inert solvent can preferably be added to the amine at the beginning of the reaction. The amine content of the mixture comprising amine and solvent is from 1 to 50, preferably from 3 to 40, percent by mass.

However, it is also conceivable to use the amine in pure form if the phosgenation is carried out in the gas phase.

The reaction mixture emerging from the reactor (reaction discharge) is generally present in the form of a suspension. This suspension contains the isocyanate to be prepared as a liquid and also undecomposed carbamoyl chlorides as solids. The suspension emerging from the reactor may furthermore contain amine hydrochlorides and/or ureas (R—NH—CO—NH—R) as solids.

The reaction discharge still contains residues of the hydrogen chloride formed in the phosgenation, the excess phosgene, the solvent and impurities and unvaporizable residue of a polymeric nature. The impurities and the polymeric residue are formed during the reaction by incomplete reaction or undesired secondary or subsequent reactions. Usually, the hydrogen chloride and phosgene are first removed in one or more steps from the reaction discharge. The solvent is then distilled off. The pure isocyanate is then prepared by the novel process from the crude isocyanate thus produced.

Alternatively, the isocyanate can also be prepared by phosgenation in the gas phase. Here, the reaction discharge, which contains the isocyanate, is quenched from the gas phase in an inert solvent. Here too, the novel process for the preparation of the pure isocyanate from the corresponding crude isocyanate after removal of hydrogen chloride, phosgene and solvent is suitable. It may be possible to effect the gas-phase phosgenation even without the use of an additional solvent. The novel process can then be applied to the crude isocyanate stream even after removal of the hydrogen chloride and phosgene.

There are usually economically relevant losses of yield during the preparation of the pure isocyanate from the crude isocyanate stream, which losses arise as a result of the desired substance, pure isocyanate, having longer residence times at relatively high temperature. The thermal stress results in oligomer formation of the isocyanate (isocyanurate, carbodiimide, uretdione, etc.), which reduces the yield. The problem of losses of yield is usually solved by carrying out the purifying distillation under greatly reduced pressure. By means of the distillation under greatly reduced pressure, the temperature level and the distillation apparatus is reduced, which reduces the tendency to polymerization. However, a disadvantage of this procedure is that the low densities in the gas phase of the distillation apparatus, owing to the greatly reduced pressure, lead to high vapor volume flow rates. High vapor volume flow rates then require large column diameters in order to maintain gas velocities which are expedient in terms of fluid mechanics in the distillation apparatus. The large column diameters are associated with undesirably high capital costs.

For the case of the preferred preparation by phosgenation, hydrogen chloride, phosgene and solvent are substantially separated off from the stream (1) to be used in the novel purification (crude isocyanate) after the preparation of the isocyanate, so that the content of hydrogen chloride and phosgene is in each case below 1 000 ppm and the solvent content is below 1, preferably below 0.5, particularly preferably below 0.1, % by weight.

The crude isocyanate stream (1) usually contains, in addition to the isocyanate to be recovered as desired product, from 100 ppm to 5% of components having a lower boiling point than the isocyanate (low boilers), from 100 to 5 000 ppm of components having a higher boiling point than the isocyanate (high boilers), the boiling point of which at atmospheric pressure is, however, not more than 60° C. higher than the boiling point of the isocyanate, and 1-8% by weight of unvaporizable residue of the polymeric nature, i.e. the product pyrolyzes before it vaporizes at atmospheric pressure.

According to the invention, in step a), the crude isocyanate stream (1) is separated by distillation under reduced pressure at from 1 to 120, preferably 1-100, mbar and at from 90 to 170° C., preferably from 100 to 160° C., in at least one theoretical plate, into a gaseous vapor stream (3) and a liquid part-stream (2). This distillation is preferably effected as a one-stage vaporization. It can be effected, for example, from a storage container and an evaporator which are operated with circulation. If desired, process step (a) can also be carried out in a column or in a part of a dividing wall column having internals with separation activity. In this case, this column or the part of the dividing wall column is operated only with a stripping section with evaporator and without rectification section and without reflux, which would be produced by condensation of the vapors, in order to meet the novel requirement b) that the unvaporizable residue in part-stream (2) is kept separate from the vapor stream (3) and/or from streams which at least partly contain the vapor stream (3).

Suitable internals with separation activity are all conventional internals which can be used in distillation columns. Internals which have a low pressure drop, such as dumped packings, structured packings or dual-flow trays, are preferred. Structured packings are particularly preferred.

The gas phase can be produced by operating an evaporator, a thin-film evaporator, a rising-film evaporator, a falling-film evaporator, a long-tube evaporator or a forced-circulation flash evaporator preferably being used. A forced-circulation flash evaporator or a falling-film evaporator is particularly preferably used.

The vapors (3) forming in step a) substantially comprise isocyanate and low boilers. However, significantly vaporizable high boilers are also concomitantly stripped by the relatively large vapor stream. Their content is as a rule below 0.5%.

The liquid part-stream (2) contains the concentrated unvaporizable residue and all other components of the crude isocyanate stream (1), and the content of low boilers is as a rule below 1, preferably below 0.5, % by weight.

The streams (2) and (3) are as a rule divided in the weight ratio 20:1-1:1, preferably 10:1-1:1, particularly preferably 8:1-4:1.

The liquid part-stream (2) is then separated from unvaporizable residue contained therein in step c), for recovery of the isocyanate contained therein. This is preferably effected in a falling-film evaporator, a rising-film evaporator, a thin-film evaporator, a long-tube evaporator, a helical tube evaporator, a forced-circulation flash evaporator or a paddle dryer, for example a Discotherm® dryer from List, or a combination of these apparatuses. The discharge is preferably fed to a thin-film evaporator, falling-film evaporator, forced-circulation flash evaporator or paddle dryer, particularly preferably a paddle dryer, very particularly preferably a paddle dryer without a cooling zone and with a discharge screw for the unvaporizable residue (8). In this process step, at least one in particular isocyanate-containing residual stream (4) in vapor form is produced.

Step c) is effected, as a rule, at 80-320° C., preferably 100-300° C., and 0.1-40, preferably 0.5-20, mbar.

The remaining residue stream (8) contains, as a rule, less than 2.5, preferably less than 1.5, particularly preferably less than 0.5, % by weight of desired product and is as a rule either highly viscous or solid and is usually incinerated or disposed of on a landfill.

The vapor stream (4) or, if a plurality of vapor streams (4) are produced, the vapor streams (4), if required after condensation, and the vapor stream (3), in gaseous form or after condensation, preferably after condensation, are then separated in a step d) by rectification into a stream (5) having a lower boiling point than the pure isocyanate, a medium-boiling stream (6) whose boiling point is close to that of the pure isocyanate, for example in the range of +/−20° C., preferably +/−10° C., particularly preferably +/−5° C., thereof, and a stream (7) which has a higher boiling point than the isocyanate.

The separation of the isocyanate-containing vapor stream (4) and of the residual stream (3) takes place in at least one distillation apparatus, preferably one or two distillation apparatuses, particularly preferably one distillation apparatus.

A possible first novel embodiment is, for example, the separation of the vapor stream (4) and of the residual stream (3) in a first distillation apparatus d1) into a high-boiling stream (7), which substantially contains high boilers, and into a further residual stream, which is separated in a further distillation apparatus d2) into the low-boiling stream (5) and into the medium-boiling pure isocyanate stream (6).

The feed to the first distillation apparatus d1) can be in vapor form or in liquid form after prior condensation. The feed is preferably effected after prior condensation in the liquid phase.

A preferred second novel embodiment is the use of a distillation apparatus d1) for separating the vapor stream (4) and the residual stream (3) into a low-boiling stream (5) and into a further residual stream, which is separated in a distillation apparatus d2) into the high-boiling stream (7) and into the medium-boiling pure isocyanate stream (6). The feed to the first distillation apparatus d1) can be effected in vapor form or after prior condensation in liquid form. The feed is preferably effected after prior condensation in the liquid phase.

In a third particularly preferred novel embodiment, the separation of the residual stream (3) and of the isocyanate-containing vapor stream (4) by distillation is effected in a distillation column having a dividing wall. The feed can be effected in vapor form or after prior condensation in liquid form. The feed of the vapor streams (4) is preferably effected after prior condensation in the liquid phase. The pure isocyanate (6) is removed on the outflow side, which is limited from the feed side by the dividing wall. The low-boiling stream (5) is taken off at the top of the column. The high-boiling stream (7) is removed at the bottom.

The distillation apparatuses are operated, as a rule, at 1-80 mbar and a bottom temperature of 100-240° C. They each have, as a rule, from 1 to 50 theoretical plates and are of a design known per se.

The two streams (4) and (3) are preferably separated together by rectification in a distillation apparatus. The separation into the three streams (5,6,7) is effected with the use of at least 2 to 50, preferably at least 8 to 30, theoretical plates. The top pressure is as a rule 4-80 mbar and the bottom temperature from 110 to 240° C. The feed of the streams (4) is preferably effected below that of the stream (3).

The streams (5) and (7) are fed to an incineration or for disposal on a landfill. The stream (5) is preferably fed for incineration.

Suitable internals with separation activity are all conventional internals which can be used in distillation columns. Internals which have a small pressure drop, such as dumped packings, structured packings or dual-flow trays, are preferred. Structured packings are particularly preferred.

If the crude isocyanate stream (1) was produced by phosgenation in a solvent having a lower boiling point than the isocyanate, the low-boiling stream (5) contains, inter alia, traces of the solvent and/or chlorine-containing impurities. If an aliphatic isocyanate is prepared, the low-boiling stream preferably contains, as the chlorine-containing impurity, a compound in which at least one isocyanate group of the desired isocyanate has been replaced by chlorine. For example, in the preparation of 1,6-diisocyanatohexane, the two chlorine-containing impurities 1-isocyanato-6-chlorohexane and 1,6-dichlorohexane result.

If the crude isocyanate stream was produced by phosgenation, the high-boiling stream contains chlorine-containing impurities and dimeric byproducts (for example carbodiimides and uretdione).

The pure isocyanate is obtainable in a purity of, as a rule, >99.4, preferably >99.5, % by weight, by the novel process.

Solvents and byproducts of the phosgenation, for example methylphenyl isocyanate in the case of TDI, phenyl isocyanate in the case of MDI and 6-chlorohexyl isocyanate and 1,6-dichlorohexane in the case of HDI, are as a rule present as low-boiling main impurities. Their content in the pure product is typically <0.5%, preferably <0.3%. High-boiling impurities which occur in particular are chlorine-containing impurities. When the invention is carried out, the content of chlorine-containing impurities having a higher boiling point than the isocyanate is typically <500 ppm, preferably <100 ppm.

Two preferred embodiments of the invention are now to be described:

FIG. 1 shows the first embodiment: For carrying out process step a), the crude isocyanate stream (1) is fed to a one-stage evaporation which consists of a container (9) and an evaporator (10) and is operated with circulation. The part-stream (2) which contains the unvaporizable residue is taken off from the container (9). The residual stream (3) is taken off in gaseous form at the top of the container (9).

For carrying out process step c), the part-stream (2) is fed, in a particularly preferred embodiment, to a paddle dryer (11) for producing the vapor stream (4).

From the paddle dryer (11), the residue stream (8), which substantially comprises unvaporizable residue, is discharged downward. The stream (4) taken off in gaseous form at the paddle dryer comprises in particular isocyanate.

The two streams (3) and (4) can be condensed in the condensers (12) and (13), respectively, and fed via the feeds (16) and (17) to a dividing wall column (14), comprising evaporator (20), condenser (22) and internals (21) with separation activity. In a particularly preferred embodiment, the stream (3) or its condensate (16) is fed in above the stream (4) or its condensate (17). The low boiler stream (5) is taken off at the top (15) of the dividing wall column (14), the pure isocyanate stream (6) is taken off on that side of the dividing wall (18) which is opposite the feed, and the high boiler stream (7) is taken off at the bottom (19).

Figure 2:
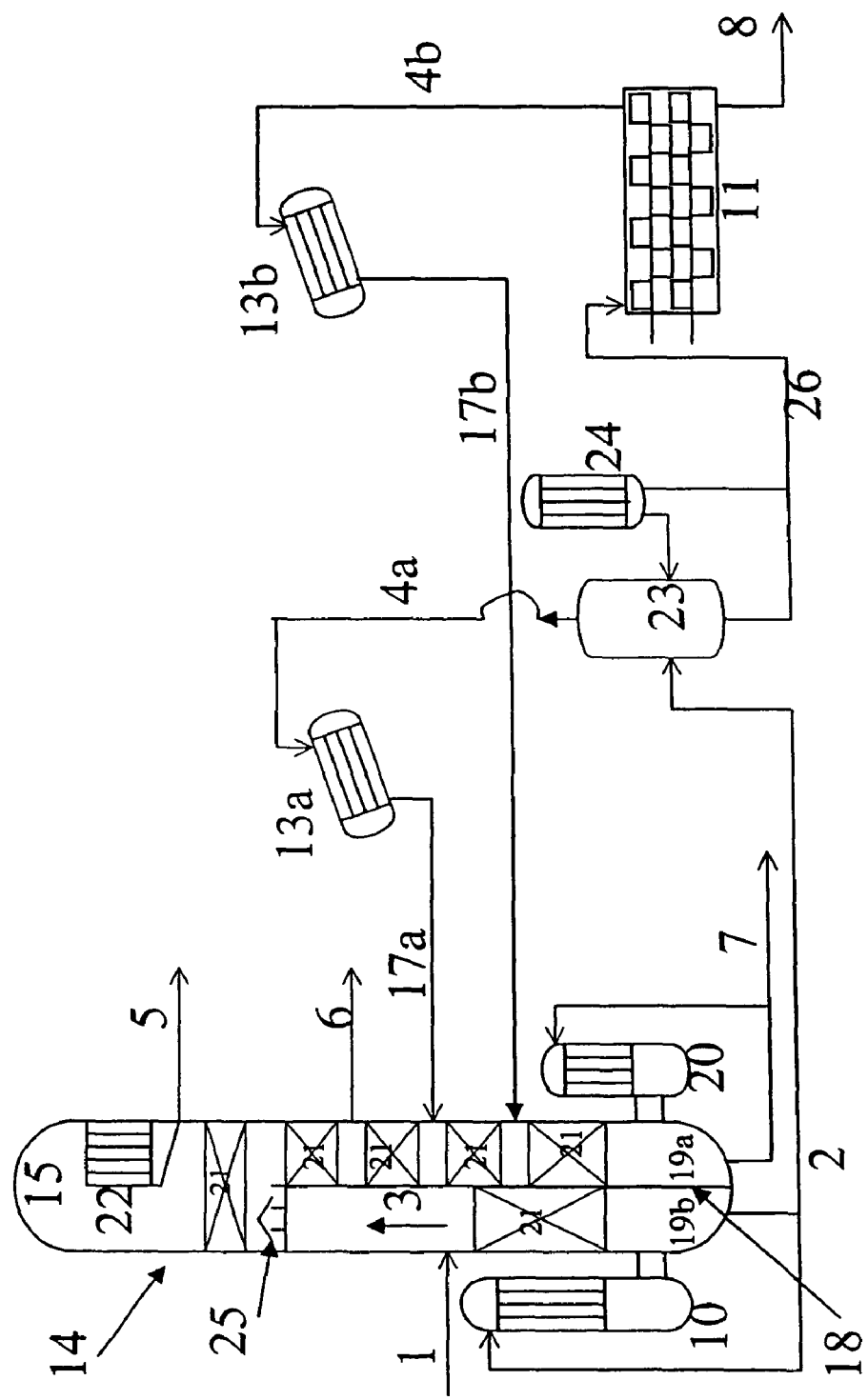
FIG. 2 is a schematic depiction of a second exemplary isocyanate purification system according to the present invention.

In the second preferred embodiment, which is shown in FIG. 2, the crude isocyanate stream (1) is initially fed to the left feed space of a dividing wall column (14) having internals (21) with separation activity. The dividing wall column (14) is designed in such a way that the dividing wall (18) continues to the base so that two separate bottoms (19a) and (19b) result. Furthermore, the dividing wall column (14) is designed in such a way that no condensate stream can flow from the condenser (22) of the dividing wall column (14) into the left feed space for the crude isocyanate stream (1).

The separation process in the feed space of the dividing wall column (14) having internals (21) with separation activity corresponds to a pure stripping distillation setup (i.e. no trays with separation activity are present above the feed (1) in the left feed space), in which the downward-falling liquid stream consists only of the feed of the crude isocyanate stream (1). The bottom of the feed space (19b) is operated with circulation with the left evaporator (10). Part-stream (2) comprising the unvaporizable residue is taken off from the bottom (19b).

The vapor stream (3) passes from the left feed space through a gas cap (25) into the remaining space of the dividing wall column without condensate entering the left feed space.

The part-stream (2) containing the unvaporizable residue is then fed to process step c). There, initially a first predominantly isocyanate-containing vapor stream (4a) is produced in a one-stage evaporation which comprises a container (23) and an evaporator (24) which are operated with circulation. The discharge stream (26) from the container (23) of this arrangement is fed to a paddle dryer (11), at the top of which a second predominantly isocyanate-containing vapor stream (4b) is obtained. The stream (8) predominantly containing unvaporizable residue is removed from the bottom of the paddle dryer.

The two isocyanate-containing streams (4a) and (4b) are condensed and fed to the dividing wall column (14).

In this embodiment, the vapor stream (3) already contains a major part of the low-boiling components and the stream (2), and the part-streams (4a) and (4b) are substantially free of low boilers. For carrying out process step d), the streams (3), (4a) and (4b) are passed into the remaining space of the dividing wall column, which space is not occupied by the left feed space. Here, this feed space is equivalent with the space below the tray with the gas cap (25) on the left side of the dividing wall column (14). Particularly preferably, the introduction of the vapor stream (3) in gaseous form is effected via the gas cap (25) above the take-off of the pure isocyanate stream (6) and the feed of the liquid, isocyanate-containing part-stream (4a) is effected below the take-off of the pure isocyanate stream (6) and the introduction of the liquid isocyanate-containing stream (4b) is effected below the introduction of the liquid, isocyanate-containing part-stream (4a).

The low boiler stream (5) is taken off at the top (15) of the dividing wall column and the high boiler stream (7) is taken off at the right bottom (19a) of the column.

Common to both preferred embodiments is the novel feature b) that the residual stream (3) or streams which at least partly contain the residual stream (3) is or are transported separately from the unvaporizable residue which is contained in part-stream (2). This is achieved in the second preferred embodiment by virtue of the fact that the dividing wall (18) of the dividing wall column (14) is continued to the base and that no condensate stream which is produced by the condenser (22) of the dividing wall column (14) and which would at least partly contain the residual stream (3) in vapor form is present above the feed of the stream (1) to the dividing wall column (14). The tray with the gas cap (25), via which the residual stream (3) in vapor form is brought into the region above the dividing wall of the dividing wall column, and which separates the feed space of the dividing wall column from the remaining part of the dividing wall column, is structurally designed according to the invention in such a way that the condensate stream produced by the condenser (22) cannot flow into the feed space of the dividing wall column (14), for example as a collecting tray.

ppm and percentage data used in this document are based on weight, unless stated otherwise.

EXAMPLE

After removal of HCl, phosgene and solvent by distillation, the tolylene diisocyanate (TDI)-containing crude isocyanate stream originating from a phosgenation of toluenediamine (TDA) was used according to the preferred embodiment of the novel process shown in FIG. 2 for the preparation of a pure TDI stream. The following conditions and flow rates resulted:

| Stream No. | Amount | Composition |
|---|---|---|
| 1 | 1 kg/h | 95% of TDI; 5% of residue (unvaporizable); 170 ppm of low boilers; 700 ppm of higher-boiling components |
| 5 | 30 g/h | 99.4% of TDI; 0.5% of low boilers |
| 6 | 0.92 kg/h | 99.9% of TDI; 10 ppm of low boilers; 50 ppm of higher-boiling components |
| 7 | 1 g/h | 30% of TDI; 70% of higher-boiling components |
| 8 | 48 g/h | 98.5% of residue; 1.5% of TDI |

| Apparatus No. | Conditions |
|---|---|
| 14 | Top pressure: 18 mbar<br>Bottom temperature (left) 19b: 145° C.<br>Bottom temperature (right) 19a: 160° C.<br>Theoretical plates (bed numbering from top to bottom)<br>Bed 1: 4 theoretical plates<br>Feed part:<br>Bed 2: 2 theoretical plates<br>Outflow part:<br>Bed 2: 2 theoretical plates<br>Bed 3: 3 theoretical plates<br>Bed 4: 2 theoretical plates<br>Bed 5: 18 theoretical plates |
| 23 | Pressure: 8 mbar<br>Temperature: 128° C. |
| 11 | Pressure: 25 mbar<br>Temperature: 240° C. |

The invention claimed is:

1. A method of purifying a product stream from isocyanate synthesis, comprising:
   separating a crude isocyanate stream into a gaseous vapor stream and a liquid part-stream by distillation;
   recovering isocyanate present in the liquid part-stream as an isocyanate-containing residual stream in vapor form;
   wherein:
   recovering isocyanate is carried out in a falling-film evaporator, a rising-film evaporator, a thin-film evaporator, a long-tube vertical-film evaporator, a helical-tube evaporator, a forced-circulation flush evaporator, a paddle dryer without cooling zone and with discharge screw for the nonvaporizable residue, or a combination thereof.

2. The method according to claim 1, wherein recovering isocyanate is carried out in the thin-film evaporator, the falling-film evaporator, the forced-circulation flush evaporator or the paddle dryer without cooling zone and with discharge screw for the nonvaporizable residue, or a combination thereof.

3. The method according to claim 1, wherein recovering isocyanate is carried out in the paddle dryer without cooling zone and with discharge screw for the nonvaporizable residue.

4. The method according to claim 1, wherein the crude isocyanate stream is obtained by phosgenation of an amine, by phosgenation of an amine hydrochloride, by phosgenation of a carbamate salt, by urea process or by reaction of a parent amine with dialkyl carbonates.

5. The method according to claim 1, wherein the crude isocyanate stream is obtained by phosgenation of an amine, by phosgenation of an amine-hydrochloride or by phosgenation of a carbamate salt.

6. The method according to claim 1, wherein the crude isocyanate stream is obtained by phosgenation of an amine.

7. The method according to claim 1, wherein the isocyanate is selected from the group consisting of monomeric methylenediphenyl isocyanate (MDI), tolylene diisocyanate (TDI), R,S-1-phenylethyl isocyanate, 1-methyl-3-phenylpropyl isocyanate, naphthyl diisocyanate (NDI), n-pentyl isocyanate, 6-methyl-2-heptane isocyanate, cyclopentyl isocyanate, hexamethylene diisocyanate (HDI), isophorone diisocyanate (IPDI), 2,4- and 2,6-diisocyanatomethylcyclohexane (H6TDI) and isomer mixtures thereof, o-, m- or p-xylene diisocyanate (XDI), diisocyanatocyclohexane (t-CHDI), di(isocyanatocyclohexyl)methane (H12MDI), tetramethyl-m-xylylene diisocyanate (m-TMXDI), 1,3-bis(isocyanatomethyl)cyclohexane (H6XDI), 1,6-diisocyanato-2,2,4,4-tetramethylhexane, 1,6-diisocyanato-2,2,4-trimethylhexane (TMDI) and mixtures thereof.

8. The method according to claim 1, wherein the isocyanate is selected from the group consisting of monomeric methylenediphenyl isocyanate (MDI), tolylene diisocyanate (DI), naphthyl diisocyanate (NDI), hexamethylene diisocyanate (HDI), isophorone diisocyanate (IPDI), 2,4- and 2,6-diisocyanatomethylcyclohexane (H6TDI) and isomer mixtures thereof, o-, m- or p-xylene diisocyanate (XDI), di(isocyanatocyclohexyl)methane (H12MDI) and diisocyanatocyclohexane (t-CHDI).

9. The method according to claim 1, wherein recovering isocyanate is carried out at a temperature of from 80 to 320° C.

10. The method according to claim 1, wherein recovering isocyanate is carried out at a pressure of from 0.1 to 40 mbar.

11. A method of purifying a product stream from isocyanate synthesis, comprising:
    separating a crude isocyanate stream into a gaseous vapor stream and a liquid part-stream by distillation;
    recovering isocyanate present in the liquid part-stream as an isocyanate-containing residual stream in vapor form;
    wherein:
    recovering isocyanate is carried out in a paddle dryer without a cooling zone and optionally including a discharge screw for non-vaporizable residue.

* * * * *